US011027145B2

(12) United States Patent
Ringeisen et al.

(10) Patent No.: US 11,027,145 B2
(45) Date of Patent: Jun. 8, 2021

(54) LASER INDUCED BALLISTIC PARTICLE IMPLANTATION TECHNIQUE

(71) Applicant: The Government of the United States of America, as represented by the Secretary of the Navy, Arlington, VA (US)

(72) Inventors: Bradley R. Ringeisen, Lorton, VA (US); Peter K. Wu, Ashland, OR (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 5 days.

(21) Appl. No.: 16/220,505

(22) Filed: Dec. 14, 2018

(65) Prior Publication Data

US 2019/0184189 A1 Jun. 20, 2019

Related U.S. Application Data

(60) Provisional application No. 62/599,171, filed on Dec. 15, 2017.

(51) Int. Cl.
*A61N 5/06* (2006.01)
*A61M 37/00* (2006.01)
*A61N 5/067* (2006.01)
*A61B 5/00* (2006.01)

(52) U.S. Cl.
CPC ............ *A61N 5/062* (2013.01); *A61M 37/00* (2013.01); *A61B 5/00* (2013.01); *A61N 2005/067* (2013.01)

(58) Field of Classification Search
CPC .......... A61N 5/062; H05B 7/00; A61M 37/00
See application file for complete search history.

(56) References Cited

U.S. PATENT DOCUMENTS

| 6,905,738 B2 | 6/2005 | Ringeisen et al. |
| 6,936,311 B2 | 8/2005 | Ringeisen et al. |
| 7,011,957 B2 | 3/2006 | Lewis et al. |
| 7,294,367 B2 | 11/2007 | Barron et al. |
| 7,381,440 B2 | 6/2008 | Ringeisen et al. |

(Continued)

OTHER PUBLICATIONS

E1, Corning Matrigel Matrix, Oct. 2020, Corning, https://www.corning.com/worldwide/en/products/life-sciences/products/surfaces/matrigel-matrix.html (Year: 2020).*

(Continued)

*Primary Examiner* — Dah-Wei D. Yuan
*Assistant Examiner* — Andrew J Bowman
(74) *Attorney, Agent, or Firm* — US Naval Research Laboratory; Joseph T. Grunkemeyer (57) ABSTRACT

A method using a receiving substrate and a target substrate having a photon-transparent support, a photon absorbent interlayer coated on the support, and a tissue-implantable particle on top of the interlayer opposite to the support. A source of photon energy is directed through the transparent support so that the photon energy strikes the interlayer. A portion of the interlayer is energized by absorption of the photon energy. The energized interlayer causes a transfer of the particle across a gap between the target substrate and the receiving substrate and embedding of the particle into the receiving substrate.

6 Claims, 9 Drawing Sheets

(56) References Cited

U.S. PATENT DOCUMENTS

| | | | |
|---|---|---|---|
| 7,875,324 B2 * | 1/2011 | Barron | A61B 18/20 427/595 |
| 8,101,247 B2 | 1/2012 | Ringeisen et al. | |
| 2003/0059866 A1 | 3/2003 | Lewis et al. | |
| 2005/0130256 A1 | 6/2005 | Lewis et al. | |
| 2007/0275451 A1 | 11/2007 | Gavrish et al. | |
| 2017/0002344 A1 | 1/2017 | Ringeisen et al. | |

OTHER PUBLICATIONS

Arnold et al., Laser Direct-Write Techniques for Printing of Complex Materials, Jan. 2007, MRS Bulletin, vol. 32, pp. 23-31 (Year: 2007).*

Ringeisen et al., "Printing Soil: A single-step high throughput method to isolate microorganisms and near-neighbor microbial sonsortia from a compex work environmental sample" Methods in Ecology and Evolution 6(2), 209-217 (2015).

* cited by examiner

Fig. 9

LASER INDUCED BALLISTIC PARTICLE IMPLANTATION TECHNIQUE

This application claims the benefit of U.S. Provisional Application No. 62/599,171, filed on Dec. 15, 2017. The provisional application and all other publications and patent documents referred to throughout this nonprovisional application are incorporated herein by reference.

TECHNICAL FIELD

The present disclosure is generally related to laser induced implantation.

DESCRIPTION OF RELATED ART

Implantation of selective molecules (Li et al., "Improved biological performance of Ti implants due to surface modification by micro-arc oxidation" *Biomaterials,* 25(14), 2867-2875 (2004)) on surfaces can modify materials properties, such as osseointegration. Implantable devices such as radiofrequency identification chips were introduced in 1998 (www.cnn.com/TECH/computing/9901/14/chipman.idg/). In the last few years, the number and complexity of implantable devices such as integrated circuit (Fekete, "Recent advances in silicon-based neural microelectrodes and microsystems: a review" *Sensors and Actuators B: Chemical* 215, 300-315 (2015)) and drug delivery systems (Meng et al., "Micro- and nano-fabricated implantable drug-delivery systems: current state and future perspectives" *Therapeutic Delivery* 5(11), 1167-1170 (2014)) have been increasing. The functions of these devices ranges from genetic modifications (Williams et al., "Introduction of foreign genes into tissues of living mice by DNA-coated microprojectiles" *Proceedings of the National Academy of Sciences of the United States of America* 88(7), 2726-2730 (1991)), drug delivery (Meng), neural stimulation (Grahn et al., "A neurochemical closed-loop controller for deep brain stimulation: toward individualized smart neuromodulation therapies" *Frontiers in Neuroscience* 8, 169 (2014)), neurochemical monitoring (Robinson et al., "Monitoring Rapid Chemical Communication in the Brain" *Chemical Reviews* 108(7), 2554-2584 (2008)), and others. The size of these implantable devices is becoming smaller; some reaching dimensions<50 µm.

The most direct method of implanting devices in a material is to make an incision on the substrate or tissue surface and bury the devices, i.e., surgical implants in tissues. (As used herein the substrate may be referred to as "tissue", though it can be any soft material.) Non-tissue applications include the formation of "smart" surgical models that may include electronic and/or optical devices and sensors. Incisions are usually much larger than the implanted device (Richter et al., "A simple implantation method for flexible, multisite microelectrodes into rat brains" *Frontiers in Neuroengineering* 6, 6 (2013)), thus creating more damage to the tissue than is necessary.

For smaller devices, <0.5 mm, implantation can be achieved using ballistics. The device to be implanted is accelerated to a high velocity and impacts the surface of the tissue. If the projectile has enough kinetic energy, it can penetrate the surface of the tissue and implant itself inside, below the surface, where it loses all of its kinetic energy and momentum. The depth of the implantation depends on the velocity of the device, contact cross-sectional area at the point of impact, hardness, and toughness of the material, and other factors. For implant sizes at the molecular level, ballistic ion-implantation is a commonly used technique. Ion implantation is done inside a vacuum chamber and is not suitable for many biological applications.

A gene gun is a commonly used tool for ballistic injection of DNA and other biomaterials into tissues. In this case, particles such as gold and tungsten are used as carrier particles. The DNA is attached to the particles and the particle is accelerated using high pressure gas. Because the carrier particles serve no function inside the tissue, they introduce unnecessary damage to the target material (Zhao et al., "Improved Biolistic Transfection of Hair Cells" *PLoS ONE* 7(10), e46765 (2012)). The high pressure pulses of He gas also produce a shock wave much larger than the size of the particles, which can cause further damage to the substrate. The size of the implants at the surface of the tissue is an area greater than 2 cm in diameter. This is not a precision implantation technique, and can cause large scale unnecessary damage to the tissue.

BRIEF SUMMARY

Disclosed herein is a method comprising: providing a receiving substrate; providing a target substrate comprising a photon-transparent support, a photon absorbent interlayer coated on the support, and a tissue-implantable particle on top of the interlayer opposite to the support; providing a source of photon energy; and directing the photon energy through the transparent support so that the photon energy strikes the interlayer. A portion of the interlayer is energized by absorption of the photon energy. The energized interlayer causes a transfer of the particle across a gap between the target substrate and the receiving substrate and embedding of the particle into the receiving substrate.

Also disclosed herein is a substrate comprising: a photon-transparent support; a photon absorbent interlayer coated on the support; and a tissue-implantable particle on top of the interlayer opposite to the support. The particle comprises an integrated circuit or a drug delivery device.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed is a pulsed-laser based technique to accelerate micro/nano scale materials and devices for implantation into tissue without the need for carrier particles. The laser-induced forward transfer (LIFT) technique is a direct writing technique. A laser pulse is shined through a laser-transparent plate, i.e., the ribbon, and focused on a film of laser-absorbing material on the other side of the ribbon. The laser energy vaporizes the material and the vapor undergoes an adiabatic expansion. The expanding gas cloud surface can reach velocities greater than 2000 m/s (Shaw-Stewart et al., "A simple model for flyer velocity from laser-induced forward transfer with a dynamic release layer" *Applied Surface Science* 258(23), 9309-9313 (2012)). If a device is attached to the surface of the laser-absorbing material, it will be accelerated by the expanding gas cloud. The final velocity of the device will be a function of many factors. Chief among these are the laser-pulse energy, the size of the laser beam, the duration of the laser pulse, the laser-absorbing material, the mass of the device, the cross-sectional area of the device as it moves through space, the ambient pressure, etc. At the correct conditions, the device can achieve the velocity needed to be implanted into a tissue or soft materials.

The rapid adiabatic expansion at a fixed energy, one laser pulse, results in a pressure wave which dissipates in a short distance, <1 mm (Mattle et al., "Shadowgraphic investigations into the laser-induced forward transfer of different $SnO_2$ precursor films" *Applied Surface Science* 278, 77-81 (2013)) from the laser-absorbing film. This means that the only damage to the tissue is when the device penetrates the tissue surface if it is >1 mm from the laser-initiated process. Materials are routinely transferred over distances much larger than 1 mm, so a process is envisioned that minimizes and/or eliminates potential tissue damage.

Particles or devices can be implanted for the treatment of wounds or tumors. Artificial sensors can be deposited to replace damaged or missing natural ones, such as in the retina. Further examples include, but are not limited to, medication delivery devices, microelectronics devices, active/passive sensors, and/or actuators implanted into skin, brain tissue, tumors, and wounded tissue to monitor cell growth/function and the healing process, administer programmed medication, stimulate/monitor nerve and growth mechanisms, identify and eliminate malignant microbes and/or monitor vital parameters such as oxygen or sugar levels.

Theoretically, the size of the focused laser pulse at the laser-absorbing material can be as small as the wavelength of the light. In practice, most common LIFT machines can easily achieve a beam size of <30 µm. Thus, 3-D patterning of implants can be achieved using direct-write techniques. X-Y or tissue surface positioning is achieved by moving the tissue or the laser beam to the appropriate location. The Z or depth positioning of the implants can be controlled by laser energy. Higher laser energies produce higher velocity of the transferred material/device and subsequently will produce deeper injection depths. Lower laser energies produce lower velocities and therefore injection at lower depths. Implantation speeds greater than 100 implants/sec can be achieved using this method, which is only limited by the motion of actuators and pulsed laser frequencies.

The transfer apparatus and methods may be any of those disclosed in U.S. Pat. Nos. 6,905,738; 6,936,311; 7,294,367; 7,381,440; 7,875,324; 8,101,247; and in US Pat. Appl. Publ. No. 2017/000234. All methods and materials disclosed therein may be used in any combination in the presently disclosed method.

Figure 1:
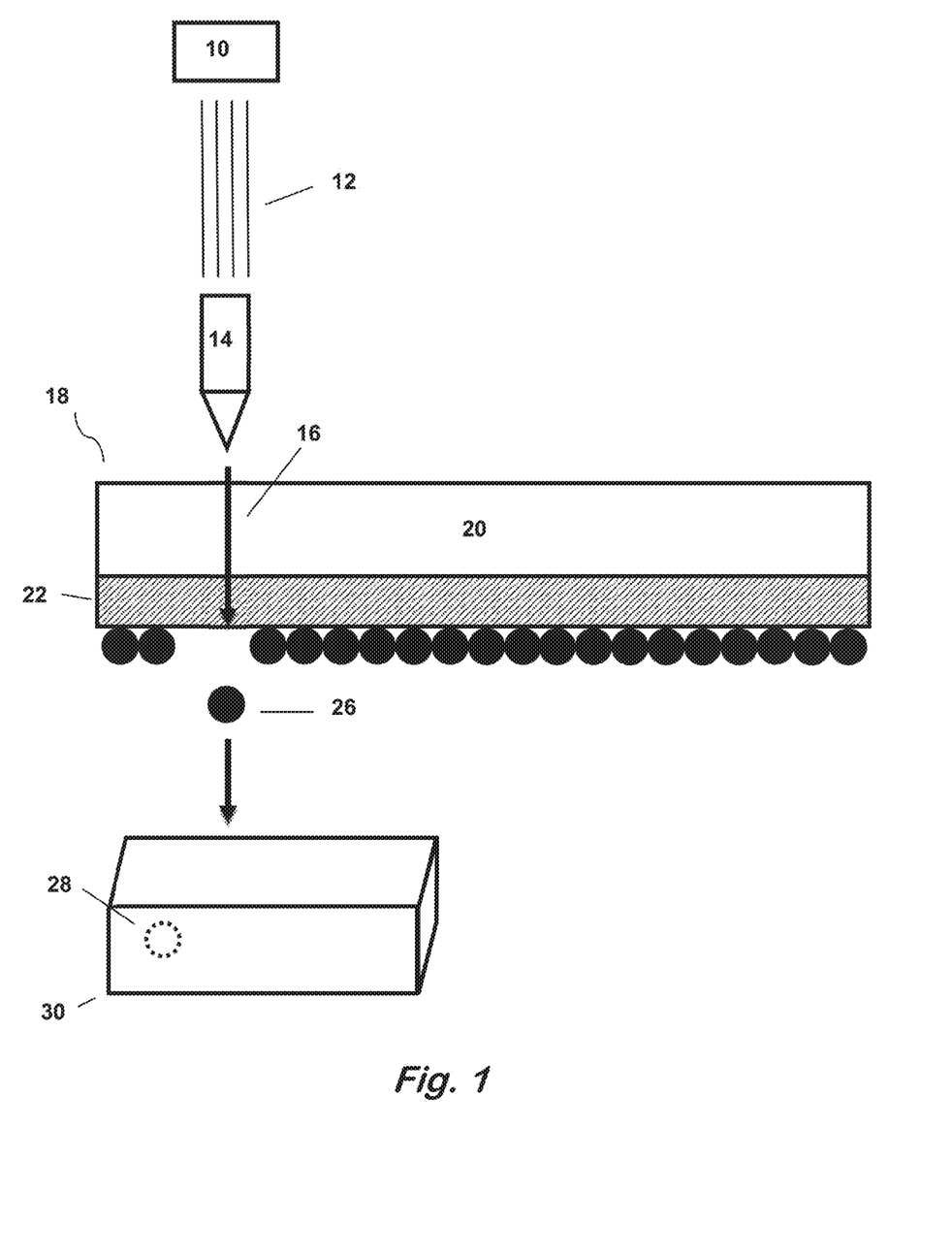
FIG. 1 schematically illustrates the transfer process.

The process is depicted in FIG. 1. A source of photon energy 10, such as a laser or flash lamp, produces photon energy 12, such as a laser beam. The beam 12 may be passed through a focusing objective 14 and through 16 a target substrate 18. The target substrate 18 has a photon-transparent support 20 or "ribbon". The ribbon is previously coated with a photon absorptive interlayer 22. Suitable materials for the target substrate 18 include quartz, sapphire, or amorphous silica for the ribbon and coated with a nm-scale (5-100 nm) titania, gold, gold alloy, platinum, or titanium as the photon absorptive interlayer.

The titania layer 22 absorbs the incident UV laser pulse 16 and initiates via a photothermal and/or photomechanical process the forward transfer of a particle 26 coated directly on top (shown in the schematic the particles are directly below the titania energy transfer layer).

The transferred particle 26 lands on a receiving substrate 30. FIG. 1 shows a particle 28 that has already been imbedded in the substrate and a second particle 26 in motion towards the substrate 30. Any of the laser, target substrate, and the receiving substrate may be independently movable in order to transfer materials from any location on the target substrate into different places on the receiving substrate.

Suitable materials for the photon transparent support include, but are not limited to, quartz, sapphire, and amorphous silica. Suitable materials for the photon absorbent interlayer include, but are not limited to, titania, gold, gold alloy, platinum, and titanium. The interlayer may be, for example, 5-100 nm thick.

Suitable particles for transfer include, but are not limited to, microbeads, particles comprising an integrated circuit, and drug delivery devices. The particle size may be, for example, up to 50 µm or up to 500 µm in diameter.

Suitable materials for the receiving substrate include, but are not limited to, a viscous liquid, a living tissue including as part of a living organism or human, an engineered tissue, and a hydrogel.

Figure 2:
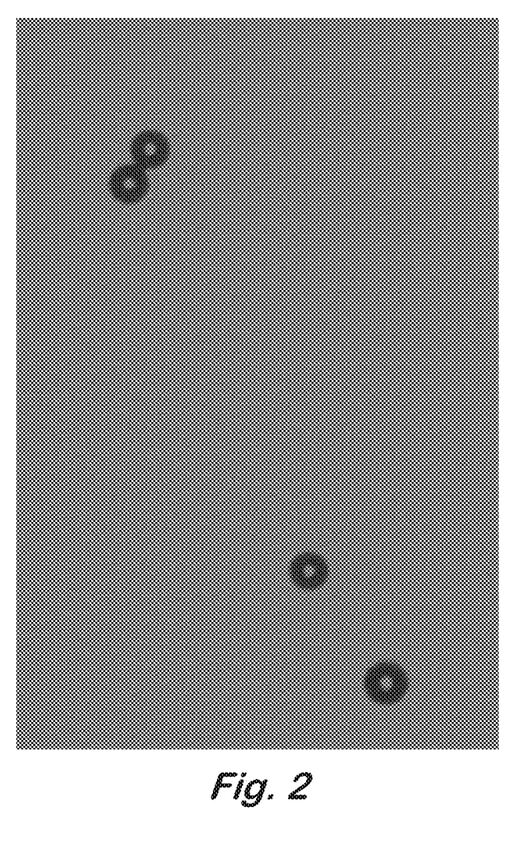
FIG. 2 shows an image of 45 µm microbeads implanted in grease.

FIG. 2 shows 45 µm diameter microbeads implanted into DOW CORNING® 1597418 grease (Jan. 14, 1915) using the disclosed technique. This demonstrates that the ballistic force from LIFT is energetic enough to penetrate a gel (model tissue) to implant devices. This deposition was done using 2 µJ/pulse of laser energy at 248 nm and $TiO_2$ as the laser-absorbing material. The penetration depth of the beads increased as the pulse energy was increased.

Figure 3:
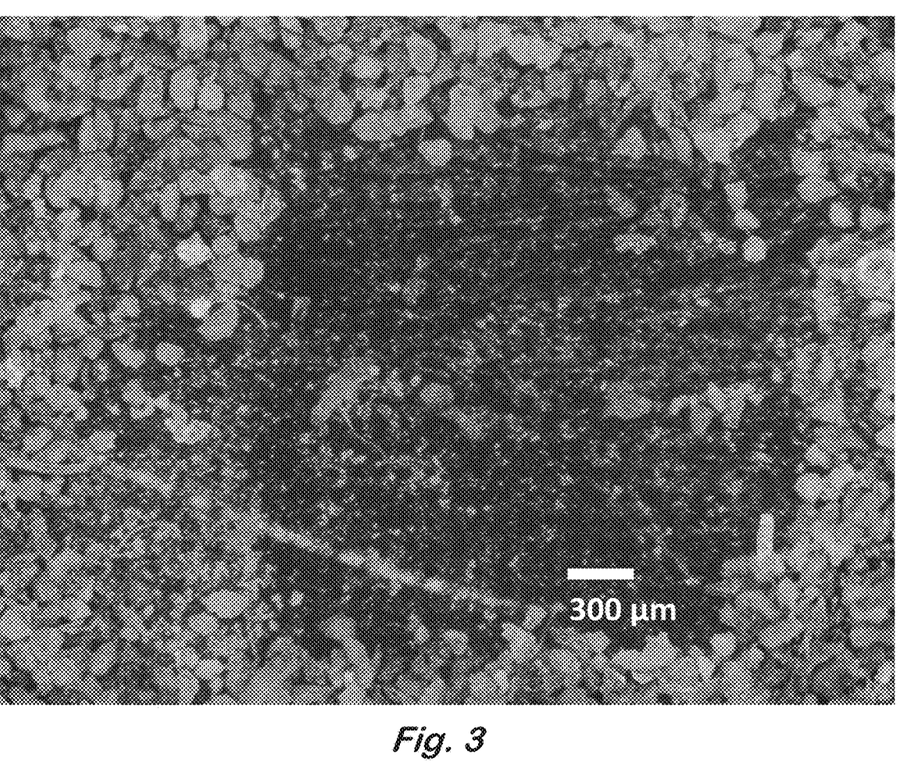
FIG. 3 shows an image of sand particles, 125-180 µm, removed ballistically from the surface of ribbon.

The size of devices that can be accelerated ballistically by this technique is shown in FIG. 3. The figure shows the ribbon after illumination by laser pulses. The laser absorbing material was $TiO_2$. The particles were sieved sand with particle sizes of 125-180 µm in diameter. The area where the laser pulse hit the $TiO_2$ layer is clearly visible as a circle. In these areas, almost all the sand particles have been ballistically removed from the ribbon. The laser energy used was 69 µJ/pulse at 248 nm.

Figure 4:
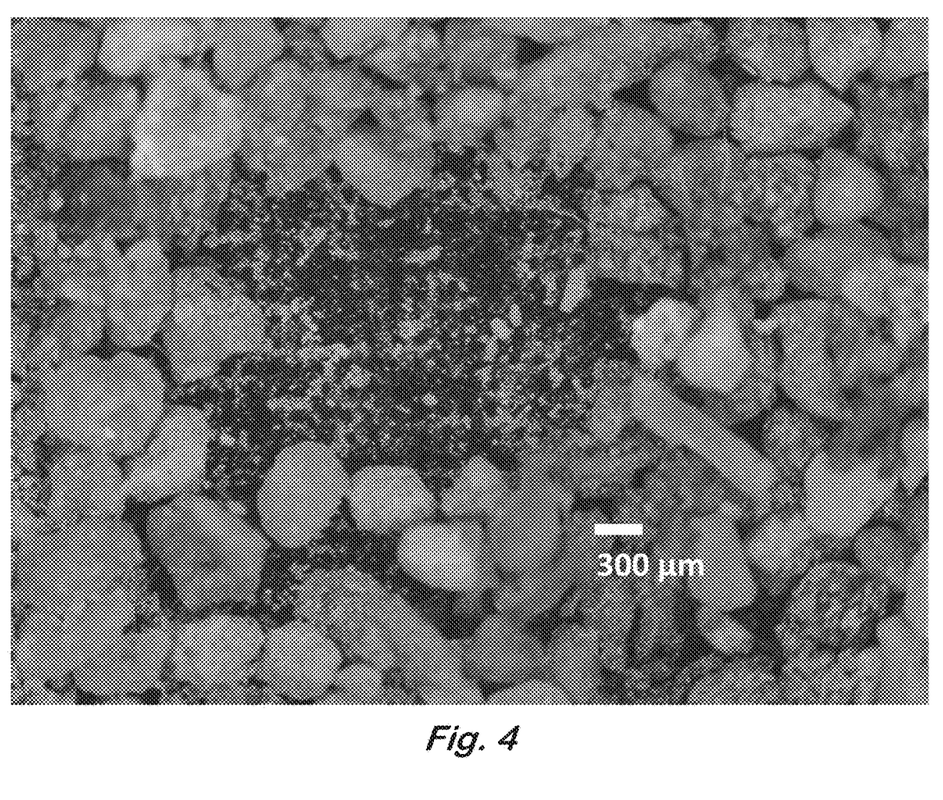
FIG. 4 shows an image of sand particles, 437-700 µm particles removed from the surface by laser pulses.
Figure 5:
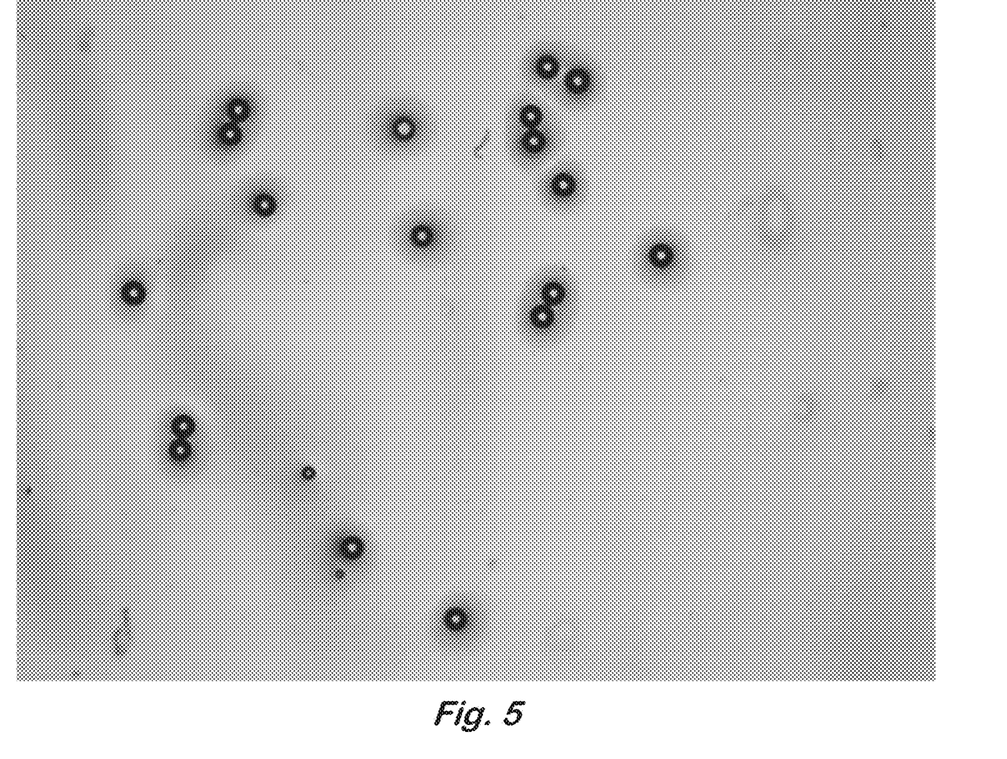
FIG. 5 shows an image of implanted 28 µm beads transferred using a 20 µJ laser pulse.
Figure 6:
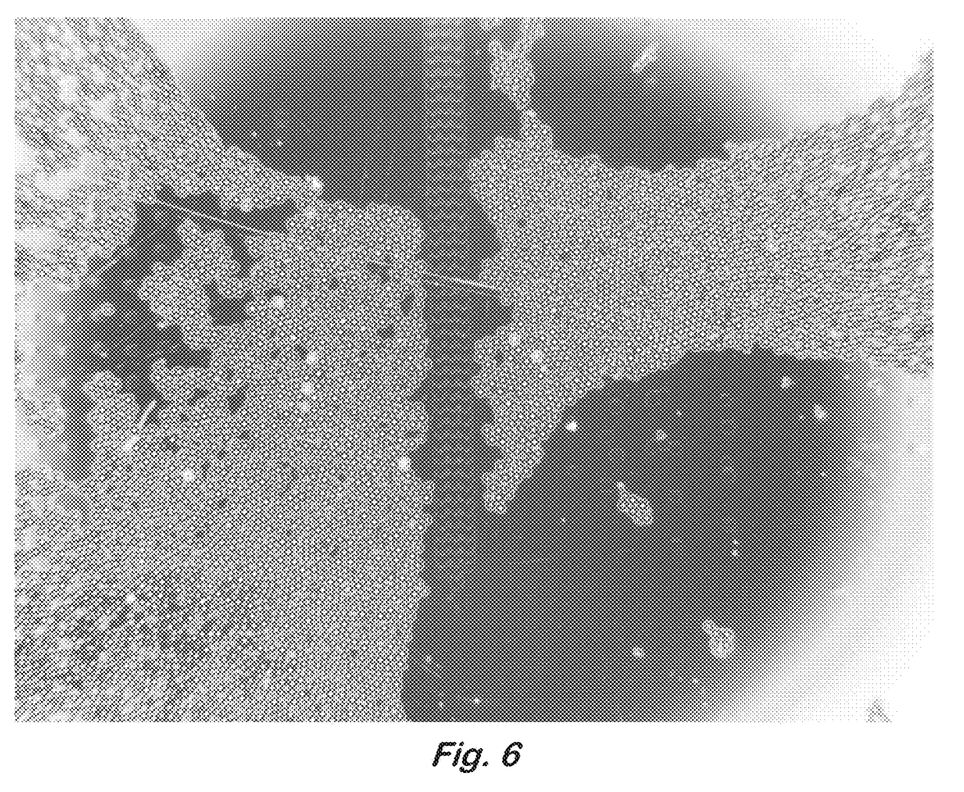
FIG. 6 shows an image of a ribbon after transfer of 28 µm beads using a 20 µJ laser pulse.
Figure 7:
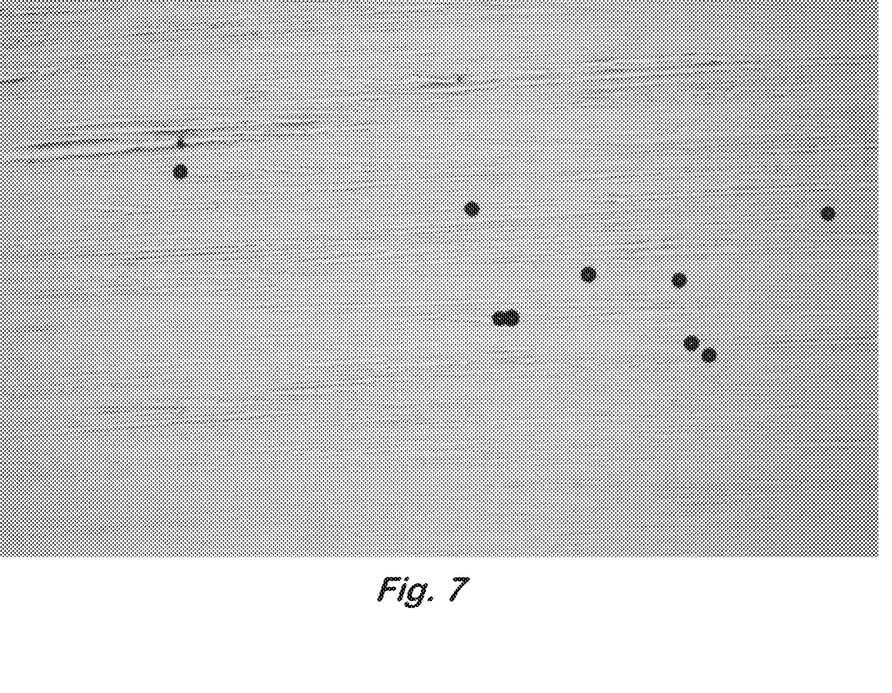
FIG. 7 shows an image of implanted 40 µm beads transferred using a 5 µJ laser pulse.
Figure 8:
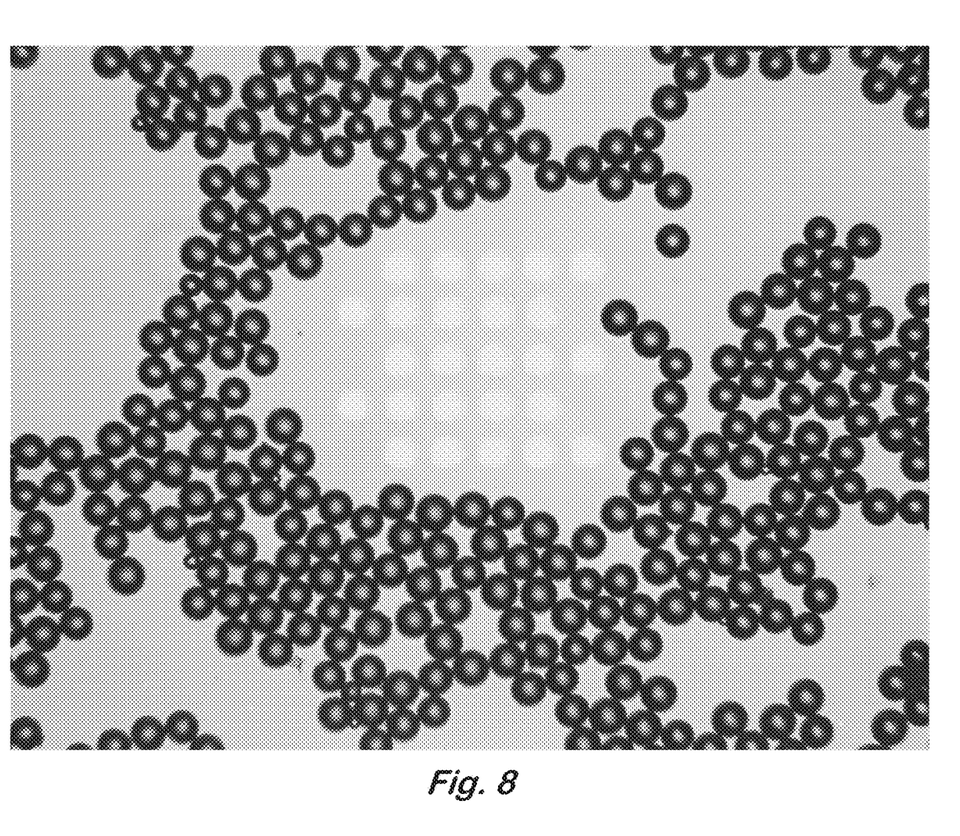
FIG. 8 shows an image of a ribbon after transfer of 40 µm beads using a 5 µJ laser pulse.

The device sizes that can be ballistically accelerated by this technique can be larger than ~100's of µm. FIG. 4 shows the ribbon after the LIFT process using laser pulses at 69 µJ/pulse at 248 nm. The sieved sand particle sizes in this case are between 437-700 µm. FIGS. 5-8 show additional images of transferred beads and ribbons after the transfer.

Figure 9:
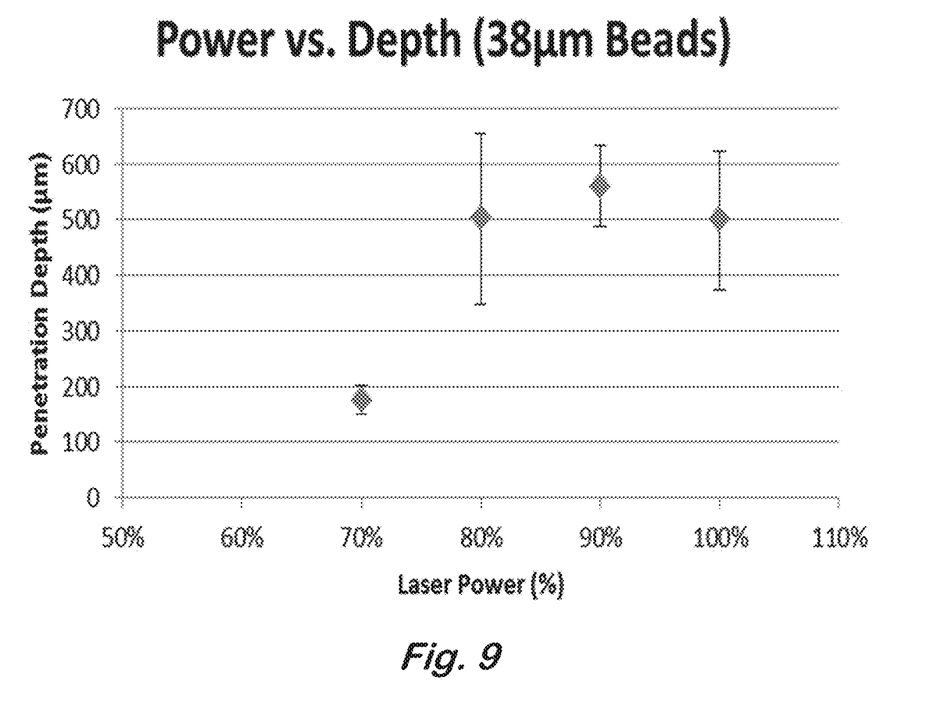
FIG. 9 shows a graph of penetration depth as a function of laser energy for 38 µm diameter beads implanted into agarose.

FIG. 9 shows a graph of penetration depth as a function of laser energy for 38 µm diameter beads implanted into agarose.

Potential advantages of the method include, that the implantation process can be visually observed by the operator in real-time, the implantation could be performed during a 3D printing process, the implantation depth can be controlled up to hundreds of microns, the non-contact mechanism eliminates contamination risks, single device/particle implantation, a device can be implanted with µm resolution anywhere on a substrate, multiple types of devices/particles can be implanted in a single operation, any implantation pattern can be created with multiple devices with µm resolution, and minimal damage to substrate Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A method comprising:
   providing a receiving substrate;
     wherein the receiving substrate comprises living tissue, a living organism, or a living human;
   providing a target substrate comprising a photon-transparent support, a photon absorbent interlayer coated on the support, and a tissue-implantable particle on top of the interlayer opposite to the support;
     wherein the particle comprises an integrated circuit;
   providing a source of photon energy; and
   directing the photon energy through the transparent support so that the photon energy strikes the interlayer;
     wherein a portion of the interlayer is energized by absorption of the photon energy; and
     wherein the energized interlayer causes a transfer of the particle across a gap between the target substrate and the receiving substrate and embedding of the particle into the receiving substrate.

2. The method of claim 1, wherein the photon transparent support comprises quartz, sapphire, or amorphous silica.

3. The method of claim 1, wherein the photon absorbent interlayer comprises titania, gold, gold alloy, platinum, or titanium.

4. The method of claim 1, wherein the photon absorbent interlayer is 5-100 nm thick.

5. The method of claim 1, wherein the particle has a diameter of no more than 500 microns.

6. The method of claim 1, wherein the particle has a diameter of no more than 50 microns.

* * * * *